United States Patent
Nie et al.

(10) Patent No.: US 6,255,050 B1
(45) Date of Patent: Jul. 3, 2001

(54) DYNAMIC HYBRIDIZATION SYSTEM

(75) Inventors: Eileen Xiao-Feng Nie; Yuan Min Wu, both of Thornhill (CA)

(73) Assignee: Lorne Park Research, Inc., Toronto (CA)

(*) Notice: Subject to any disclaimer, the term of this patent is extended or adjusted under 35 U.S.C. 154(b) by 0 days.

(21) Appl. No.: 09/083,409

(22) Filed: May 22, 1998

(Under 37 CFR 1.47)

(51) Int. Cl.⁷ .................................................. C12Q 1/68

(52) U.S. Cl. ........................... 435/6; 435/6; 435/287.1; 435/91.1; 536/24.3; 935/78; 935/85; 204/450; 204/456; 216/39; 424/256.1; 424/282.1; 424/193.1; 424/192.1; 424/185.1; 423/324

(58) Field of Search ........................... 435/6, 287.2, 91.1; 536/24.3; 935/78, 85; 204/450, 456; 216/39; 423/324; 424/256.1, 282.1, 193.1, 192.1, 185.1

(56) References Cited

U.S. PATENT DOCUMENTS

| | | |
|---|---|---|
| 4,220,450 | 9/1980 | Maggio . |
| 4,469,863 | 9/1984 | Ts'o et al. . |
| 4,787,963 | * 11/1988 | MacConnell .................. 204/180.1 |

(List continued on next page.)

FOREIGN PATENT DOCUMENTS

| | | |
|---|---|---|
| 0 232 967 | 8/1987 | (EP) . |
| 512334 | 11/1992 | (EP) . |
| 599337 | 6/1994 | (EP) . |
| 781853 | 7/1997 | (EP) . |
| WO 89/11100 | 11/1989 | (WO) . |
| WO 92 18650 | 10/1992 | (WO) . |
| WO 93 24652 | 12/1993 | (WO) . |
| 94/12665 | 6/1994 | (WO) . |
| WO 94 25477 | 11/1994 | (WO) . |
| WO 95/27081 | 10/1995 | (WO) . |
| 96/34983 | 11/1996 | (WO) . |
| WO 97 12995 | 4/1997 | (WO) . |
| 99/00902 | 5/1999 | (WO) . |

OTHER PUBLICATIONS

Perry–O'Keefe et al., "Peptide Nucleic Acid Pre–Gel Hybridization: An Alternative to Southern Hybridization," 93 Proc. Natl. Acad. Sci. USA 14670 (Dec. 1996).

Smulevitch et al., "Enhancement of Strand Invasion by Oligonucleotides Through Manipulation of Backbone Charge," 14 Nature Biotechnology 1700 (Dec. 1996) (disclosed in Landsdorp, "Close Encounters of the PNA Kind," 14 Nature Biotechnology 1653 (Dec. 1996)).

Lansdrop, "Close Encounters of the PNA Kind," 14 Nature Biotechnology 1653 (Dec. 1996).

Egholm et al., "PNA Hybridizes to Complementary Oligonucleotides Obeying the Watson–Crick Hydrogen–Bonding Rules," 365 Nature 566 (1993).

Tomac et al., "Ionic Effects on the Stability and Conformation of Peptide Nucleic Acid Complexes," 118 J.Am.Chem..Soc. 5544 (1996).

Coghlan, "One–step DNA test in a tube," New Scientist, p. 21 (Nov. 5, 1994).

(List continued on next page.)

Primary Examiner—Carla J. Myers
(74) Attorney, Agent, or Firm—Caesar, Rivise, Bernstein, Cohen & Pokotilow, Ltd.

(57) ABSTRACT

Rapid methods and means for hybridizing DNA, RNA and analogs thereof are provided. Hybridization occurs on a partition assembly through which nucleobase-containing sequences are driven by a force, such as centrifugal force, electrophoretic force, gravitational force vacuum force and/ or pressure. The unbound sequences hybridize with complementary sequences bound to the partition assembly. The force applied to drive the sequences through the partition assembly increases the rate of hybridization by increasing the rate of collisions between complementary sequences.

31 Claims, 10 Drawing Sheets-

U.S. PATENT DOCUMENTS

| | | |
|---|---|---|
| 4,963,477 | 10/1990 | Tehen . |
| 5,100,775 | 3/1992 | Smyczek et al. . |
| 5,142,047 | 8/1992 | Summerton et al. . |
| 5,166,315 | 11/1992 | Summerton et al. . |
| 5,166,330 | 11/1992 | Engels et al. . |
| 5,217,592 | 6/1993 | Jones . |
| 5,217,866 | 6/1993 | Summerton et al. . |
| 5,223,618 | 6/1993 | Cook et al. . |
| 5,310,650 | 5/1994 | McMahon et al. . |
| 5,332,659 | 7/1994 | Kidwell . |
| 5,405,938 | 4/1995 | Summerton et al. . |
| 5,470,974 | 11/1995 | Summerton et al. . |
| 5,501,949 | 3/1996 | Marshall . |
| 5,503,980 | 4/1996 | Cantor . |
| 5,521,063 | 5/1996 | Summerton et al. . |
| 5,538,848 | 7/1996 | Livak et al. . |
| 5,541,307 | 7/1996 | Cook et al. . |
| 5,587,469 | 12/1996 | Cook et al. . |
| 5,594,138 | 1/1997 | Dykstra et al. . |
| 5,601,831 * | 2/1997 | Green et al. ............... 424/256.1 |
| 5,602,240 | 2/1997 | De Mesmaeker et al. . |
| 5,610,289 | 3/1997 | Cook et al. . |
| 5,618,704 | 4/1997 | Sanghvi et al. . |
| 5,623,065 | 4/1997 | Cook et al. . |
| 5,632,957 | 5/1997 | Heller et al. . |
| 5,661,028 * | 8/1997 | Foote et al. ............... 435/287.2 |
| 5,674,698 | 10/1997 | Zarling et al. . |
| 5,677,437 | 10/1997 | Teng et al. . |
| 5,747,247 | 5/1998 | Kowalczykowski et al. . |

OTHER PUBLICATIONS

"PNA Oligomers as Hybridization Probes," vol. 1, Issue 2 of PerSeptive Biosystems Magazine, 1995.

Heppell–Parton, "Gene Mapping by Fluorescence in Situ Hybridization," p. 350–54, in *Molecular Biology and Biotechnology: A Comprehensive Desk Reference* (Myers, ed. 1995).

Rawls, "Optimistic About Antisense," 75(22) Chem. Eng. News 35, 39 (Jun. 2, 1997).

Matthews et al., "Analytical Strategies for the Use of DNA Probes," 169 Analytical Biochemistry 1 (1988).

R. Hogrefe et al., Nucleic Acids Research, 1993, vol. 21:2031–2039.

Jensen et al., "Kinetics for Hybridization of Peptide Nucleic Acids (PNA) with DNA and RNA Studied with the BIAcore Technique," 36(16) Biochem. 5072 (Apr. 1997).

Carlsson C. et al., "Screening for Genetic Mutations," Nature, 380:207, Mar., 1996.

Grunstein et al., "Colony Hybridization: A Method for the Isolation of Cloned DNAs that Contain a Specific Gene," Proc. Nat'l Acad. Sci., 72(10):3961–3965, 1975.

Meinkoth et al., "Hybridization of Nucleic Acids Immobilized on Solid Supports," Analytical Biochemistry, 138:267, 1984.

Thomas, "Hybridization of Denatured RNA and Small DNA Fragments Transferred to Nitrocellulose," Proc. Nat'l Acad. Sci., 77(9):5201–5205, 1980.

Wetmur, Biopolymers, 14:2517–2524, 1975.

Chang et al., Biopolymers, 13:1847–1858, 1974.

Zhang et al., "Single–base mutational analysis of cancer and genetic diseases using membrane bound modified oligonucleotides," 19(14) Nucleic Acids Research 3929–3933 (Jul. 25, 1991).

Cooper et al., "Analysis of fluorescent energy transfer in duplex and branched DNA molecules," 29 Biochemistry 9261 (1990).

Cardullo et al., "Detection of nucleic acid hybridization by nonradiative fluorescence resonance energy transfer," 85(23) PNAS USA 8790 (1988).

* cited by examiner

DYNAMIC HYBRIDIZATION SYSTEM

FIELD OF THE INVENTION

This invention relates to nucleic acid hybridization and detection, and more particularly to methods and means for hybridizing complementary nucleic acid molecules at an accelerated rate.

BACKGROUND OF THE INVENTION

The use of nucleic acid probes to detect particular target nucleic acid sequences in samples containing at least one nucleic acid is of vast utility to research, medicine and forensics. Because nucleic acid probes are highly specific for their target sequences, they can be used as diagnostic reagents to detect the presence of a particular nucleic acid, as well as features within that nucleic acid. Commercial nucleic acid probe assays are being developed for the detection of infectious microorganisms, viruses, mutations in the human genome, as well as for fingerprinting human and other species' genomes. Research applications of nucleic acid probes are many, having been extensively utilized in recombinant DNA work for over 10 years.

Nucleic acid probe hybridization involves the detection of a target nucleic acid (e.g., RNA or DNA), either bound to a solid support or free in solution, using a labeled complementary probe nucleic acid or analog thereof (e.g., peptide nucleic acids (PNAs), methylene methyl amino oligonucleotides, and other polymers having Watson-Crick bases). Nucleic acid probe assays fall into two general categories, i.e., free-solution (or homogeneous) assays and solid support (or heterogeneous) assays.

In homogeneous assays, the target and probe nucleic acids are dissolved in solution. Target nucleic acid is first extracted from the sample, typically denatured to convert it to single-stranded form, and dissolved in hybridization buffer. Extraction of target nucleic acid from the sample and denaturation thereof can be accomplished by the procedure disclosed by Maniatis et al. in "Molecular Cloning: A Laboratory Manual", Cold Spring Harbor Laboratory (1982), pages 191 to 198. A labeled probe complementary to the target nucleic acid is added to this solution and allowed to hybridize with the target sequence. When the hybridization reaction is complete, a suspension of hydroxyapatite (calcium hydroxide) is added. The hydroxyapatite selectively binds double-stranded probe/target nucleic acid duplexes as well as other double-stranded molecules, but does not bind unannealed single-stranded molecules. The insoluble hydroxyapatite with probe/target sequence duplex bound thereto is separated from the hybridization medium by centrifugation and washed to remove traces of unreacted probe molecules. If the probe has an isotopic label, the amount of probe bound to the hydroxyapatite is quantitated by scintillation counting. Other conventional means can be used to detect and quantitate nonisotopically labeled probe bound to the hydroxyapatite.

Heterogeneous assays can be performed in many ways. A particularly common method comprises binding a single-stranded target nucleic acid to a nitrocellulose or nylon filter in an irreversible manner. This can be accomplished by applying the target nucleic acid to the filter, and then baking them at temperatures of 70° C. to 80° C. for about one to about two hours under reduced pressure, i.e., at a pressure of less than 1 psi. The filter with sample nucleic acid bound thereto is subsequently prehybridized by immersion in an aqueous solution containing salts, protein, nonreactive DNA or RNA, sodium dodecyl sulfate detergent, buffer, EDTA, and formamide to block nonspecific binding sites on its surface. See, e.g., Grunstein et al, "Colony Hybridization: A Method for the Isolation of Cloned DNAs that Contain a Specific Gene," Proc. Nat'l Acad. Sci., 72(10):3961–3965, 1975.

When the prehybridization step is complete, labeled probe is dissolved in an aqueous solvent and is added to the solution containing the prehybridized filter to which the sample nucleic acid is bound. The probe is allowed to hybridize with the filter-bound sample nucleic acid until formation of sample/probe duplexes has gone to completion. The filter is then removed from the hybridization solution and washed with a buffered salt solution at a controlled temperature to remove nonspecifically bound labeled probe sequences. After the washing step, only labeled probe molecules which are specifically annealed to matching sample target sequences remain on the filter. The washed filter can be autoradiographed, or other appropriate conventional means can be used to detect the label and determine the amount and location of the bound probe, and thereby the location of the complementary sample sequences originally applied. See, e.g., Meinkoth et al., "Hybridization of Nucleic Acids Immobilized on Solid Supports," Analytical Biochemistry, 138:267, 1984; and Thomas, "Hybridization of Denatured RNA and Small DNA Fragments Transferred to Nitrocellulose," Proc. Nat'l Acad. Sci., 77(9):5201–5205, 1980.

All nucleic acid probe assays require a step in which a labeled probe nucleic acid is hybridized to a target nucleic acid sequence. The time required for such hybridization is often a critically limiting factor in nucleic acid probe assays. The rate of hybridization is affected by several factors, such as ionic strength, temperature, concentration of the reactant molecules, and the presence of denaturing solvent. Concentration of the reactant molecules is perhaps the most important of these factors, because it limits the rate at which the random collisions between the complementary nucleic acid probe and target sequences occur as required to bring about hybridization. Once two complementary nucleic acid molecules have appropriately collided, they rapidly hybridize to form a thermodynamically stable duplex that does not spontaneously dissociate into its single-stranded components.

It has been found that the rate of DNA or RNA hybridizaton in homogeneous assays can be accelerated by the addition to the hybridization medium of water soluble polymers, such as dextran sulfate, polyvinyl pyrrolidone, or tetraethyl ammonium chloride. See, e.g., Wetnur, Biopolymers, 14:2517–2524, 1975; Chang et al., Biopolymers, 13:1847–1858, 1975; and Kohne, ACPR:20–29, November 1986. The mechanism by which these polymers enhance the rate of hybridization of DNA or RNA molecules is believed to involve a reduction in the effective solvent volume available to the nucleic acids in solution. The negatively charged polymers complex with available solvent molecules from around the nucleic acid molecules, resulting in an effective increase in concentration of DNA or RNA molecules relative to each other. Such concentration is believed to be effective to increase the number of collisions between complementary sequences, and to thereby produce faster hybridization rates.

Such rate-enhancing compounds have been found to increase nucleic acid probe hybridization rates by 10 to 200 fold in homogeneous assays, thereby making possible hybridization times of 1 to 2 hours, rather than overnight. In the case of short synthetic nucleic acid probes, hybridization reactions can be completed in less than 15 minutes if high concentrations of oligomeric probe, for example 1 milligram per milliliter, are used along with rate-enhancing compounds. In general, however, the hybridization reaction for nucleic acid probe assays requires 1 to 2 hours when probes of 100 or more nucleotides in length are used in homogeneous hybridization assays. Moreover, rate-enhancing compounds have not been found to significantly enhance the hybridization rate for heterogeneous assays.

In order to supply the frequent need of researchers and others to collect a dense amount of nucleic acid molecules, for example on a carrier membrane, instruments are available commercially which can separate nucleic acid from a gel or can isolate or concentrate nucleic acid molecules from a solution thereof. The operation of such electroelution or electrophoretic concentration devices takes advantage of the fact that, due to the presence of phosphate groups on the nucleic acid backbone, DNA and RNA in aqueous solution are highly negatively charged molecules. When a voltage is applied across platinum wire electrodes placed in a solution of RNA or DNA, the resulting current flow through the solution causes the negatively charged nucleic acid molecules to migrate toward the positive electrode (anode) and concentrate on its surface.

In the aforementioned commercial devices, this principle is used to electrophoretically concentrate the migrating DNA or RNA molecules from a solution, or from agarose or acrylamide containing such molecules, onto the surface of a liquid permeable, for example a cellulose, collector membrane which is impermeable to the nucleic acid molecules and is positioned to prevent such molecules from contacting the anode. Usually, devices of this sort are configured with two chambers separated by the membrane. In one chamber the gel or nucleic acid-containing moiety is placed in a buffered solution near but not against one side of the membrane. The second chamber contains only buffered solution in contact with the other side of the membrane so that aqueous solution contacts both sides of the latter. Platinum wire electrodes present in the respective chambers are connected to a constant direct voltage power supply, the electrode in the chamber containing the nucleic acid to be concentrated being connected to the negative terminal of the source to provide a cathode, and the other electrode being connected to the positive terminal thereof to provide an anode. The electric potential impressed across the electrodes by the source, causes current flow through the aqueous solutions and is effective to cause the negatively charged nucleic acid molecules in the cathode chamber electrophoretically to migrate toward and be concentrated onto the side of the membrane or disc exposed in the cathode chamber. The nucleic acid becomes deposited on the membrane or disc during the procedure. Upon completion of the concentration step, the electrodes are disconnected from the source, and the nucleic acid deposited on the membrane can be easily removed therefrom, as by washing.

Depending upon the type of membrane used therein, the commercial devices can also be used to bind to the membrane the nucleic acids concentrated thereon. For example, when a membrane of modified nylon is used, the nucleic acids concentrated thereon are bound thereto upon contact. On the other hand, when a membrane of nitrocellulose is used, the nucleic acids concentrated thereon can be bound thereto upon removal of the membrane from the instrument. Such binding can be accomplished by baking at a temperature of 70° C. for about one to about two hours at reduced pressure, i.e. less than 1 psi.

Examples of commercial electrophoretic concentration/elution instruments of the type discussed above are the Electro-Eluter/Concentrator available from CBS Scientific, Del Mar, Calif. 92014; the preparative gel electrophoresis system available from Bethesda Research Laboratories, Bethesda, Md.; and the Trans-Blot Cell available from Bio-Rad, Richmond, Calif.

U.S. Pat. No. 4,787,963 to MacConnell discloses methods and means for hybridizing complementary nucleic acid molecules at an accelerated rate by electrophoretically moving unhybridized probe sequences successively in various directions along the surface of a nucleic acid impermeable membrane and in contact with the target sequences bound thereto. The rate of hybridization is increased due to an increase in the incidence of collisions between probe and target molecules.

MacConnell discloses performing electrophoretically-enhanced hybridization on a membrane assembly sandwiched between opposing solutions. It does not disclose a method of enhancing hybridization by applying electrophoretic force to a membrane within a gel.

U.S. Pat. No. 5,632,957 to Heller et al. discloses systems for performing molecular biological diagnoses, including nucleotide hybridization assays. The systems have a matrix of addressable microscopic locations on their surfaces, wherein each location is able to electronically control and direct the transport and attachment of specific binding entities (e.g., nucleic acids) to the locations, thereby increasing the rate and specificity of hybridization by concentrating hybridization reactants at specific microscopic locations. Any un-bound analytes or reactants can be removed by reversing the polarity of a micro-location.

Heller et al. at column 16, lines 16–18, discloses the use of "convective mass transport" as an alternative method to its preferred method of electrophoretic transport.

U.S. Pat. No. 5,310,650 to McMahon et al. discloses a method for assaying nucleotides on porous media, particularly microporous chromatographic media. The method increases the rate of hybridization by using capillary action to enhance interaction of probe and target.

None of the foregoing patents disclose centrifugation-enhanced and vacuum-enhanced hybridization methods. Moreover, it is unclear from the foregoing patents whether any of the methods are sensitive enough to distinguish a one-base mismatch from a perfect match between probe and target. Many applications require such sensitivity, particularly when a one-base mutation is all that distinguishes wild-type DNA and mutant-type DNA which is correlated with disease.

All references cited herein are incorporated herein by reference in their entireties.

SUMMARY OF THE INVENTION

The present invention provides a method for rapidly hybridizing nucleobase-containing sequences, said method comprising:

providing a partition assembly having first nucleobase-containing sequences bound thereto;

exposing said partition assembly to unbound second nucleobase-containing sequences;

applying a force to drive said unbound second nucleobase-containing sequences through said partition assembly; and hybridizing said unbound second nucleobase-containing sequences to said bound first nucleobase-containing sequences to form hybridization complexes.

The invention additionally provides a method for assaying nucleobase-containing sequences, said method comprising:

providing a partition assembly having first nucleobase-containing sequences bound thereto;

exposing said partition assembly to unbound second nucleobase-containing sequences;

applying a force to drive said unbound second nucleobase-containing sequences through said partition assembly;

hybridizing said unbound second nucleobase-containing sequences to said bound first nucleobase-containing sequences to form hybridization complexes;

separating non-specifically binding second nucleobase-containing sequences which remain unhybridized from said hybridization complexes and said partition assembly;

de-hybridizing said hybridization complexes to release second nucleobase-containing sequences therefrom;

collecting said de-hybridized second nucleobase-containing sequences in a liquid medium;

irradiating said collected sequences in said liquid medium with a laser beam to excite fluorophores attached to said collected sequences to emit fluorescent radiation; and detecting said fluorescent emission to assay for said second nucleobase-containing sequences.

The invention also provides a hybridization method comprising:

thermally denaturing first nucleobase-containing sequences;

cooling said denatured sequences to about 0° C.; and hybridizing said denatured and cooled first nucleobase-containing sequences to second nucleobase-containing sequences, wherein said cooling is sufficiently rapid to maintain said first nucleobase-containing sequences in substantially denatured form for said hybridization.

Also provided are systems for practicing methods of the invention, said systems comprising:

a partition assembly comprising at least one permeable or semi-permeable partition, wherein nucleobase-containing probe sequences (or target sequences) are bonded to said at least one partition and said at least one membrane is sufficiently porous to allow targets (or probes) to pass therethrough;

force-generating means for driving said targets (or probes) through said partition assembly;

a laser for inducing fluorophores on said targets (or probes) to fluoresce;

a fluorescence detector;

a data recorder; and a data display device.

BRIEF DESCRIPTION OF THE DRAWINGS

The invention will be described in conjunction with the following drawings in which like reference numerals designate like elements and wherein.

DEFINITIONS

Figure 1:
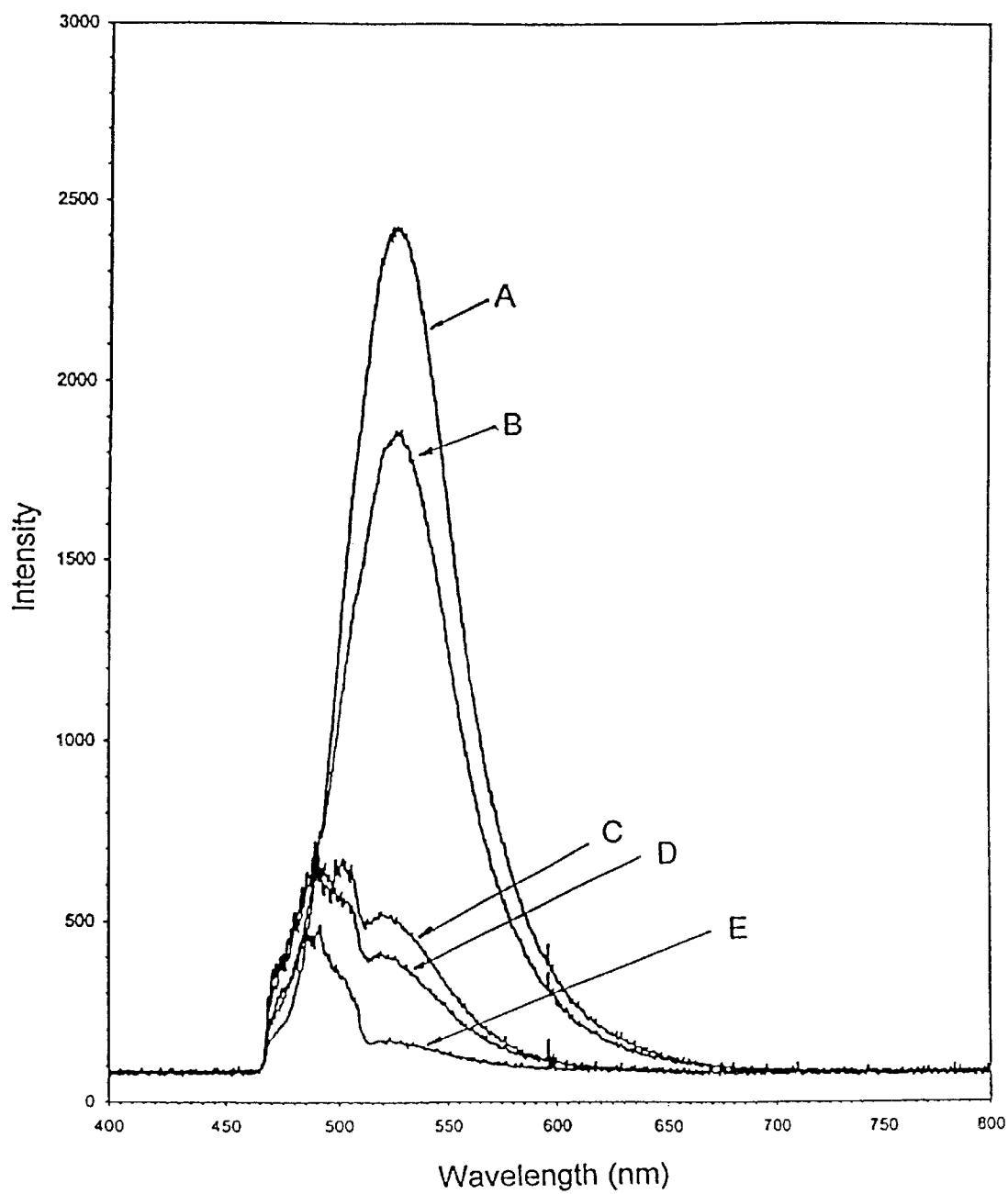
FIGS. 1, 2, 3, 4, 5, 6, 7, 8, 9 and 10 are fluorescent spectra.

Although the terminology employed herein generally conforms to conventional usage, the following definitions are provided to remove any doubt as to the meaning of selected terminology employed to help define the limits of the invention.

The expression "nucleobase-containing sequence" as used herein encompasses, e.g., DNA, RNA, modified nucleic acid sequences (e.g., methylphosphonated oligonucleotides) and PNA. The term is intended to encompass all molecules capable of specifically hybridizing via base pairing to complementary (or partially complementary) segments of DNA and/or RNA.

The term "de-hybridization" as used herein means separating the members of a hybridization complex. That is, de-hybridization is the reverse of hybridization.

The term "partition assembly" as used herein encompasses one or more of any permeable or semi-permeable partition device through which a fluid can be driven, such as, e.g., membranes, filters, colanders, screens, sieves, strainers, and the like.

DETAILED DESCRIPTION OF PREFERRED EMBODIMENTS

The invention provides methods and means for rapidly hybridizing nucleobase-containing sequences to one another. The rate of hybridization is increased without any apparent decrease in specificity or sensitivity. The rapid hybridization methods of the invention can be employed in a variety of methods, including separation, sequencing and assay methods.

The methods of the invention employ a partition assembly having nucleobase-containing sequences loaded thereon. The sequences loaded on the partition assembly can be either target sequences or probe sequences, with probe sequences being preferred for binding to the partition assembly.

The partition assembly can comprise, e.g., one or more membranes. The membranes should be sufficiently porous to permit the free nucleobase-containing sequences (i.e., the sequences to be bound to the immobilized sequences) to pass therethrough. Suitable pore sizes are preferably on the order of about 0.025 microns to about 10 microns, more preferably about 0.1 microns to about 1 micron.

Non-limiting examples of suitable components of the partition assembly include membranes fabricated of nylon (e.g., a Biodyne C membrane, available from Pall Corporation, Port Washington, N.Y.) or other polymers, glass, or other porous materials. Suitable commercially available membranes in addition to the Biodyne C membrane, include, e.g., the Biodyne A, B and plus membranes available from Pall Corporation, and Nitrocellulose and Immobilon Affinity membranes available from Millipore Corp. (Bedford, Mass.).

Those of ordinary skill in the art will appreciate that the nature of the membrane (or other partition device) is dictated to a certain extent by the nature of the nucleobase-containing sequences bound thereto, and by the desired method of linking the sequences to the membrane.

A single membrane or a plurality of membranes can be used in the partition assembly of the invention. When a plurality of membranes (and/or other partition devices) are used, they can be directly in contact with one another, or separated from one another.

In a preferred embodiment of assaying according to the invention, a first membrane is placed on a second membrane, wherein the first and second membranes have been loaded with two distinct types of nucleobase-containing sequences, each type providing different information regarding a target sequence. The membranes can be separated after hybridization and separately analyzed. For example, the first membrane can be loaded with a probe for a sequence that only occurs in a mutant-type DNA, while the second membrane is loaded with a probe for a sequence that occurs in both the mutant-type DNA and wild-type DNA. The second membrane acts as a positive control for the assay. Negative assay controls could also be employed in place of, or in addition to, positive assay controls.

The membranes can be in direct contact with one another, or spaced from one another across an empty or media-filled volume.

Prior to hybridizing complementary sequences, the partition assembly is loaded with nucleobase-containing sequences and activated by conventional methods. These methods are typically specified by the manufacturer of the partition device(s) in the assembly.

For example, the Biodyne C membranes preferably used in conjunction with the invention are preferably activated with 1-ethyl-3-(dimethylamino propyl)-carodiimide hydrochloride (EDC), immersed in sodium bicarbonate buffer containing oligonucleotide sequences to be immobilized, incubated, washed with buffer, quenched with 0.1 N sodium hydroxide, washed with deionized water and dried. A suitable method for covalently binding nucleobase-containing sequences to the Biodyne C membrane is described in Zhang et al., "Single-base mutational analysis of cancer and genetic diseases using membrane bound modified oligonucleotides," 19(14) Nucleic Acids Research 3929–3933 (Jul. 25, 1991).

The nucleobase-containing sequences bonded to the partition assembly can be targets or probes for the unbound nucleobase-containing sequences, with the unbound sequences being the complementary probes or targets. The target sequences and probe sequences need not be the same type of polymer and are not particularly limited, provided that they contain nucleobase sequences that are sufficiently complementary to specifically hybridize under the hybridization conditions employed. For example, the probes can be any molecule that specifically hybridizes to its complement via Watson-Crick base pairing, such as, e.g., single-stranded PNA (ssPNA), DNA, RNA, modified nucleotides, etc., while the targets can be ssDNA, double-stranded DNA (dsDNA), RNA, etc. The targets and probes need not be perfectly complementary, and in certain assaying embodiments, information provided by mismatched couplings is useful.

Preferred targets can be from 18 bases to 1 kb in length. Preferred probes can be from 8 to 40 bases in length, with lengths of 10 to 20 bases being most preferred.

Conventional hybridization media can be employed in the methods of the invention. The partition assembly is immersed in a hybridization solution, a buffer, a gel, or another medium, and contacted with unbound nucleobase-containing sequences.

In the alternative damp hybridization method of the invention, the partition assembly can be moistened with conventional hybridization media containing the probe (or target). The limited volume of media containing the probe (or target) is driven back and forth through the partition assembly using, e.g., vacuum or pressure.

As discussed above, the rate of hybridization is enhanced in the method of the invention by employing a driving force to enhance the rate of collisions between target and probe. Driving forces found to be suitable for this purpose, include, e.g., electrophoretic force, centrifugal force, gravitational force, vacuum force and/or pressure.

In certain embodiments employing electrophoretic force, the partition assembly is inserted into a gel containing unbound nucleobase-containing sequences. Electrophoretic force is applied to drive the unbound sequences through the gel and partition assembly. Preferably, the unbound sequences are driven forward and back through the partition assembly at least once (i.e., the unbound sequences pass through the partition assembly at least twice) by reversing the polarity of the electrophoretic force between passages.

It is preferable to maintain the gel temperature at about 32° C. during the method. Maintaining the voltage at less than about 5 v/cm assists in this regard.

In certain embodiments employing centrifugal force, the partition assembly is inserted into a container suitable for holding the assembly and a solution containing unbound nucleobase-containing sequences, and suitable for centrifuging (e.g., a microspin column available from Pharmacia Biotech, Uppsala, Sweden). The unbound nucleobase-containing sequences are driven through the partition assembly by centrifuging the container, preferably at about 500 g to about 750 g for about 15–60 seconds. Preferably, this centrifugation step is repeated at least once, and not more than eight times (further repetitions yield diminishing returns). It is also preferred to maintain the temperature of the centrifuger at room temperature (i.e., about 22° C.).

Suitable centrifugers are not particularly limited, and include, e.g., the Eppendorf 5810R microcentrifuger (Brinkmann Instrument, Westbury, N.Y.).

Other suitable driving means for driving unbound probe/target through the partition assembly include, e.g., applying a vacuum pressure differential across the partition assembly. This can be accomplished by, e.g., attaching a vacuum to one end of the container holding the partition assembly. The direction of the driving force can be repeatedly reversed to drive the unbound probe/target through the partition assembly a plurality of times.

The sufficiency of hybridization and/or the progress of the hybridization reaction can be monitored in real time by, e.g., comparing the strength of a signal obtained from the medium before each cycle with the signal strength from the medium after each cycle. When the signal strength of the medium remains substantially constant through a cycle, the hybridization reaction is complete. Thus, for example, hybridization can be considered to be complete when the fluorescent intensity of the hybridization buffer after a centrifugation cycle is substantially the same as it was before the cycle.

After the unbound nucleobase-containing sequences have been driven through the partition assembly sufficiently, the assembly is separated from the media in which it and the unbound sequences were contained. This step helps to separate bound hybridization complexes from any unbound nucleobase-containing sequences which remain unhybridized (the unbound nucleobase-containing sequences will sometimes hereinafter be referred to as targets, although in less preferred embodiments, they can be probes).

The partition assembly is then washed (preferably with deionized water) to remove any targets non-specifically adhering thereto.

It is preferred to then release hybridized targets from the partition assembly by immersing it in a solution suitable to de-hybridize the hybridization complexes. For the Biodyne C membrane, a 0.2 N sodium hydroxide solution is suitable to denature the nucleobase-containing sequences, thus releasing (or "de-hybridizing") the targets. Preferably, the membrane is immersed in 100 µl of 0.2M NaOH for about 10 minutes. The resulting solution can be collected for analysis.

The membrane or other partition device can then be recycled for further use. Theoretically, there is no limit on the number of times the partition assembly could be reused. However, as a practical matter, mechanical damage to the partition assembly would probably limit the number of times it can be recycled. A partition assembly could, perhaps, be recycled about 5 to 20 or more times without substantially losing its effectiveness.

A signal correlated with the concentration of target in the solution can be induced and/or monitored to assay for the target. Preferably, the solution is collected in a cuvette and analyzed according to the fluorescence-based methods disclosed in our earlier U.S. patent application Ser. Nos. 08/807,901; 08/870,370; and 08/886,280.

Thus, the preferred markers for use in assays of the invention are fluorophores, which are preferably bound to the unbound nucleobase-containing sequences before hybridization (i.e., to the probe or target that is not bound to the partition assembly). The fluorophores are preferably excited to fluoresce by laser irradiation. As will be appreciated by the skilled artisan, the wavelength preferably selected to excite fluorescence of the fluorescent marker is known in the art as the "excitation maximum," i.e., that wavelength which is absorbed by a molecule and excites that molecule to a higher electronic state. When the marker molecule passes from the higher to a lower electronic state, the molecule emits a type of visible radiation, i.e., fluorescence, at a wavelength referred to as the "emission maximum." It is this fluorescence that is preferably detected in the present invention.

The detectable signal emitted by the compound can be detected using techniques known in the art, for example, by observation with the human eye, using electronic means for detecting a generated wavelength (e.g., cameras and CCDs), and the like. Advantageously, the wavelength of fluorescence is sufficiently removed from that of the exciting light to allow good separation of the two wavelengths by optical filters.

The excitation wavelength is selected (by routine experimentation and/or conventional knowledge) to correspond to this excitation maximum for the marker being used, and is preferably 400 to 1000 nm, more preferably 400 to 750 nm. For example, when the marker is fluorescein, the preferred wavelength of excitation is about 488 nm.

In preferred embodiments, an argon ion laser is used to irradiate the marker with light having a wavelength in a range of 400 to 520 nm, and fluorescent emission is detected in a range of 500 to 750 nm. The duration of irradiation is preferably about 10 milliseconds to about 1 minute.

As with our prior applications, it is not only possible to detect whether hybridization has occurred, but it is also possible to detect the nature of the hybridization. As shown in the examples below, the detection methods are sufficiently sensitive to distinguish a solution obtained from a one base pair mismatched hybridization complex from a solution obtained from a perfectly matched hybridization complex. The fluorescent intensity detected is proportional to the concentration of label in the solution. The amount of label in the solution is proportional to the amount of target released from the partition assembly. The amount of target on the partition assembly is proportional to the hybridization efficiency between the target and the probe. Thus, the intensity of a solution obtained from a mismatched hybridization complex is lower than the intensity of a solution obtained from a perfectly matched hybridization complex.

The fluorescent intensity can be calibrated against known concentrations of known solutions that are analyzed separately or together with the test solution.

For example, two membranes can be used in the partition assembly—the first loaded with probes perfectly complementary to a target sequence and the second loaded with probes imperfectly complementary to the target sequence. The membranes can be treated as described above and then tested for hybridization. If the fluorescent intensity of the solution from the first membrane is less than or equal to the intensity of the solution from the second membrane, then the target sequence has not been detected.

In an assay for the presence of one of two possible sequences, probes perfectly complementary with a segment of the first sequence can be loaded on the first membrane and probes perfectly complementary with a segment of the second sequence can be loaded on the second membrane. The first sequence is detected if the fluorescent intensity of the resulting solution is greater than the intensity of the solution from the second membrane, and vice-versa.

In certain embodiments, probes and targets are not de-hybridized prior to detection. The labeled hybridization complexes generate a signal proportional to their concentration on the partition assembly, enabling the targets to be assayed without de-hybridizing the probes and targets.

Suitable fluorophores can fluoresce at frequencies higher than the frequency of excitation (i.e., they can act as up-converting labels, such as those disclosed in U.S. Pat. No. 5,674,698 to Zarling et al.), or at frequencies lower than the frequency of excitation.

Detection can be accomplished without providing a signal quenching agent on the labeled sequence, without the use of enzymes, and without significant electronic interaction between multiple labels on each labeled sequence.

The invention will be illustrated in more detail with reference to the following Examples, but it should be understood that the present invention is not deemed to be limited thereto.

EXAMPLES

Sequence synthesis

Two 18mer oligonucleotides with 5'-amino group linkers, Probe-1 and Probe-2, were synthesized by a DNA synthesizer (Expedite 8909, PerSeptive Biosystems). Phosphoroamidites and synthesis reagents were purchased from PerSeptive Biosystems. Amino group linker (5'-amino modifier C6-TFA) and spacer (Spacer Phosphoramidite 18—DMT-C-C-O-C-C-O-C-C-O-C-C-O-C-C-O-C-C-O-P-N(iPr)$_2$) were purchased from Glen Research (Sterling, Va.). Synthesis was conducted according to the specified protocols of the manufacturers. Target DNA, ssDNA-1 and ssDNA-2 were also synthesized using the same apparatus and protocols. In particular, the following sequences were synthesized (wherein the abbreviation "Fluo" represents fluoroscein):

Probe-1: 5'-amino-spacer-CCT CAT TCA GCT CTC GGA (SEQ ID NO:1)

Probe-2: 5'-amino-spacer-CCT CAT TCT GCT CTC GGA (SEQ ID NO:2)

ssDNA-1: 5'-Fluo-TCC GAG AGC TGA ATG AGG (SEQ ID NO:3)

ssDNA-2: 5'-Fluo-TCC GAG AGC AGA ATG AGG (SEQ ID NO:4)

ssDNA-3: 5'-Fluo-TCC GAG AGA AGA ATG AGG (SEQ ID NO:5)

ssDNA-4: 5'-Fluo-TCC GAG AGT ACA ATG AGG (SEQ ID NO:6)

ssDNA-5: 5'-Fluo-TCC TCT CCC CAG CCA AAG (SEQ ID NO:7)

Membrane Preparation

Biodyne C membranes were cut into circular plates having diameters of about 6 mm. Each plate was acidified by rinsing with 0.1 M hydrochloric acid. Each membrane was pre-activated by immersion in 1 M 1-ethyl-3-(dimethylamino propyl)-carodiimide hydrochloride (EDC) for 15 minutes at room temperature. The membrane was then immersed in a 0.5 M sodium bicarbonate buffer containing 10 $\mu$M probes and incubated for one hour. After washing away unbound oligonucleotides with PBS/Tween buffer and deionized water, each membrane was quenched with 0.1 N NaOH solution for 10 minutes. Finally, each membrane was washed with deionized water and dried by air for immediate application, or stored at $-20°$ C.

Target DNA can be driven through a membrane by electrophoresis in a buffer, centrifugation, gravity, vacuum, pressure, other mechanical forces, or combinations of the foregoing forces.

Centrifugation

A membrane having Probe-1 or Probe-2 bonded thereto was placed into a microspin column. The membrane was exposed to target DNA, which was driven through the membrane by a microcentrifuger for about one minute. The hybridization temperature was maintained at 22° C.

Electrophoresis

After agarose or polyacrylamide gels were set, a membrane was inserted into a gel at an incision provided about 3 cm from the wells. 200 pmol of target DNA with a fluorescent tag were driven forward and backward through the membrane for six to eight times (i.e., passed through the membrane three to four times) by electrophoresis. During electrophoresis, the temperature of gel and buffer were maintained at 32° C. by maintaining the voltage under about 5 volts/cm.

Post-hybridization

After hybridization, the membrane was washed twice with deionized water. The membrane was then immersed into 100 $\mu$l of 0.2 M NaOH for 10 minutes to denature the sequences. The resulting solution was transferred to a cuvette for fluorescent analysis according to our earlier applications, discussed above.

Examples 1A–1E

In each of Examples 1A–1E, Probe-1 was covalently bound to a membrane. 10 $\mu$l of a 100 pmol solution of ssDNA target sequence and 40 $\mu$l 0.5×TBE buffer were added on the membrane, then centrifuged ten times through the membrane.

The following target sequences were used in the Examples:

Example 1A ssDNA-1
Example 1B ssDNA-2
Example 1C ssDNA-3
Example 1D ssDNA-4
Example 1E ssDNA-5

FIG. 1 shows the results from Examples 1A–1E. Intensity is proportional to the hybridization efficiency, which is inversely proportional to the number of mismatches between the target and probe sequences. Thus, the perfectly matched probe and target of Example 1A generated a solution having the highest intensity (as measured at about 525 nm after laser irradiation at about 488 nm); the one base mismatched pair of Example 1B yielded the second highest intensity; the two base mismatched pair of Example 1C yielded the third highest intensity; the three base mismatched pair of Example 1D yielded the fourth highest intensity; and the unmatched pair of Example 1E yielded the lowest intensity.

These results demonstrate that the invention provides a rapid and sensitive method for assaying nucleobase-containing sequences, and for readily distinguishing between very similar molecules differing by as little as a single base.

Examples 2A–2C

In Examples 2A–2C, membranes were prepared as follows:

Example 2A Probe-1
Example 2B Probe-2
Example 2C No Probe (negative control)

10 $\mu$l (100 pmol) ssDNA-1 target sequence and 40 $\mu$l 0.5×TBE buffer were added on each membrane, then centrifuged ten times through the membrane.

Figure 2:
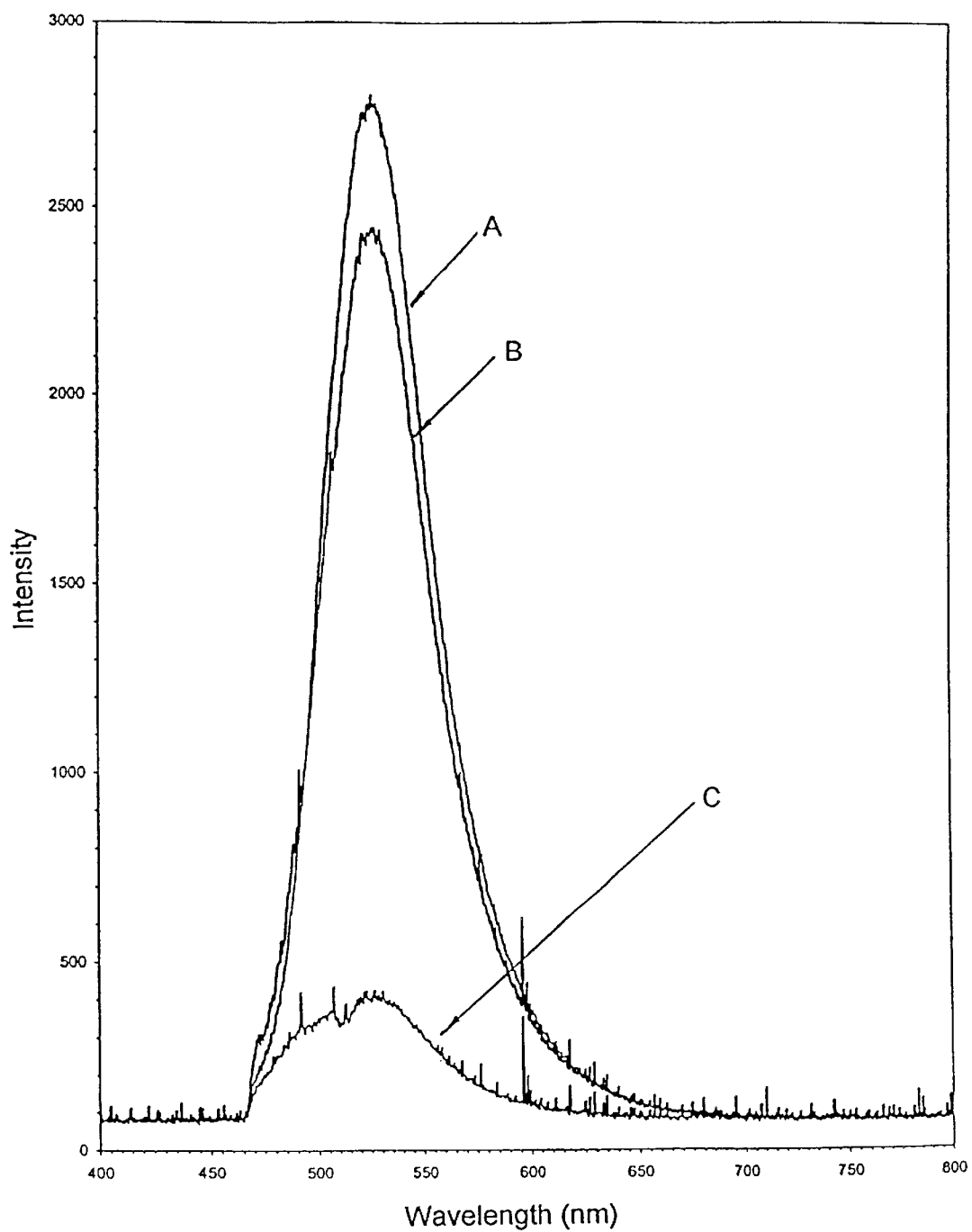

FIG. 2 shows the results of ssDNA-1 hybridization on membranes covalently bound with different probes. The perfectly matched pair of Example 2A yielded the highest intensity; the one base mismatched pair of Example 2B yielded the second highest intensity; and the negative control of Example 2C yielded the lowest intensity by far.

Examples 3A–3C

In Examples 3A–3C, membranes were prepared as follows:

Example 3A Probe-2
Example 3B Probe-1
Example 3C No Probe (negative control)

10 $\mu$l (100 pmol) ssDNA-2 target sequence and 40 $\mu$l 0.5×TBE buffer were added on each membrane, then centrifuged ten times through the membrane.

Figure 3:
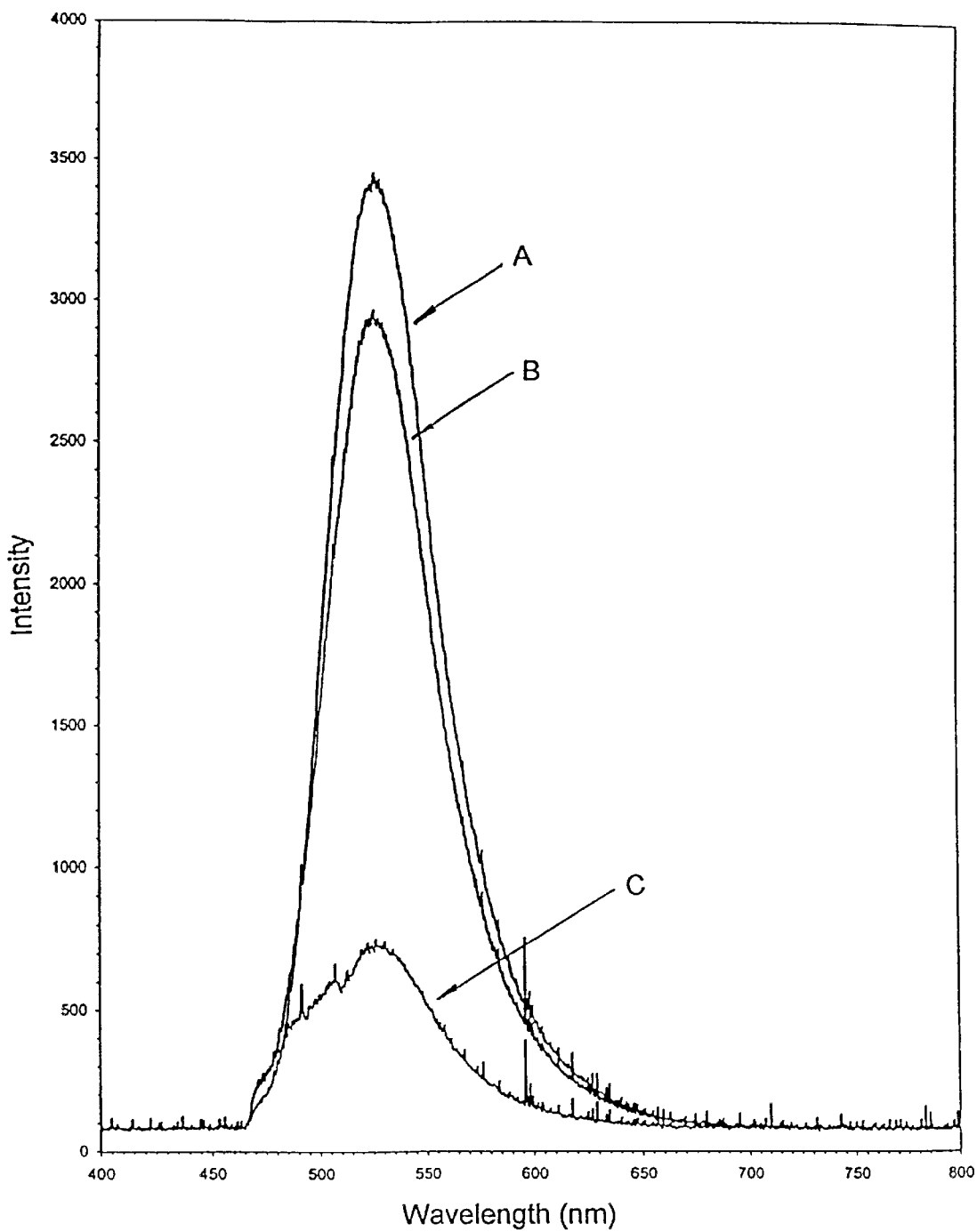

FIG. 3 shows the results of ssDNA-2 hybridization on membranes covalently bound with different probes. The perfectly matched pair of Example 3A yielded the highest intensity; the one base mismatched pair of Example 3B yielded the second highest intensity; and the negative control of Example 3C yielded the lowest intensity by far.

Example 4

In this example, two membranes were used in a partition assembly for simultaneous hybridization in the same container. The top membrane of the partition assembly was covalently bound with Probe-1 and the bottom membrane of the partition assembly was covalently bound with Probe-2. 10 $\mu$l (100 pmol) ssDNA-1 and 40 $\mu$l 0.5×TBE buffer were added on the partition assembly, then centrifuged through the partition assembly 10 times. After hybridization, the membranes of the partition assembly were separated for separate analysis.

Figure 4:
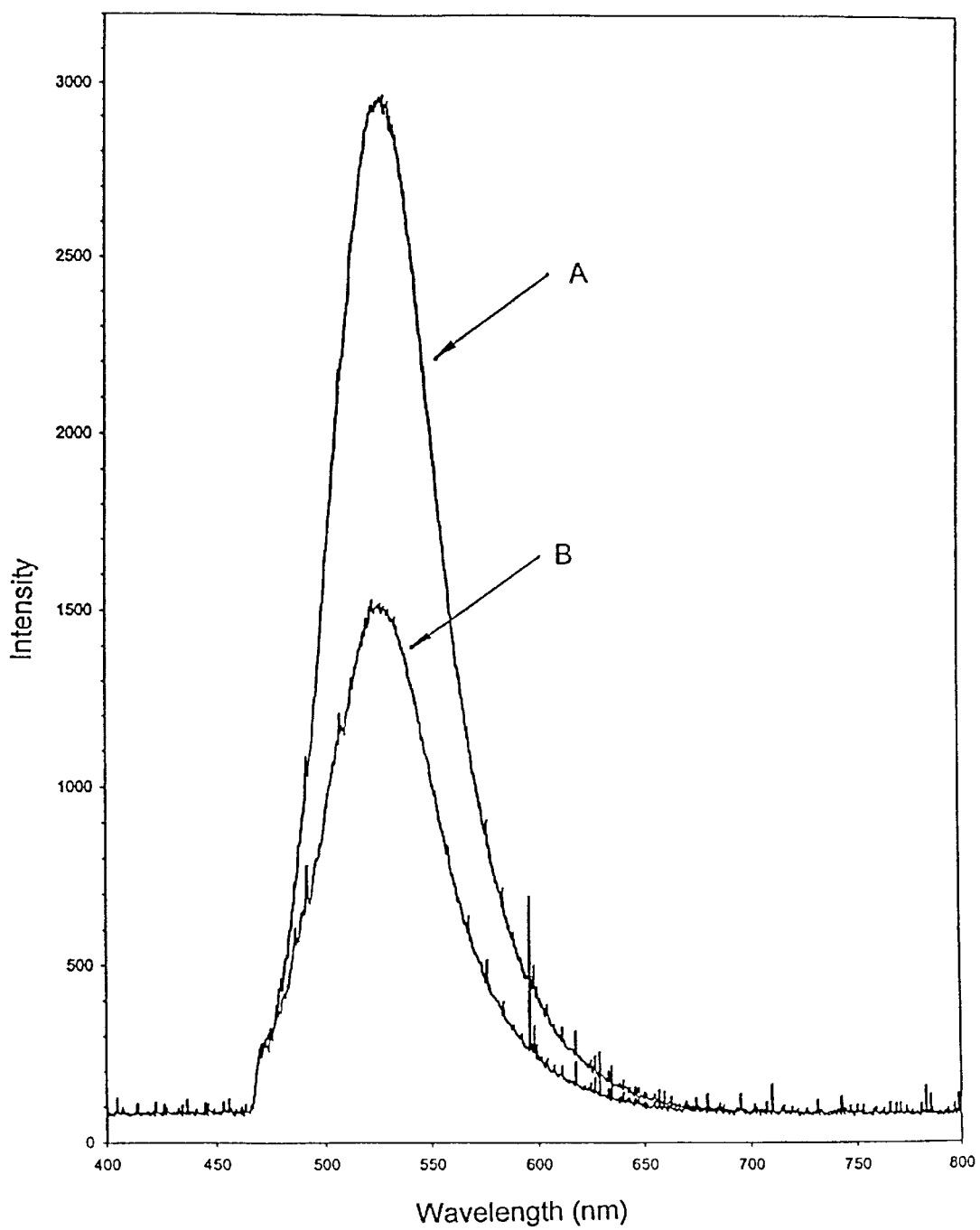

FIG. 4 shows the results of ssDNA-1 hybridization on the double-layer partition assembly. Curve A corresponds to the solution obtained from the top membrane and Curve B corresponds to the solution obtained from the bottom membrane. The peak intensity of Curve A (perfect match) is nearly double that of Curve B (one base mismatch).

Example 5

Example 5 was identical with Example 4, except that the membranes in the partition assembly were reversed—the top membrane was covalently bound with Probe-2 and the bottom membrane was covalently bound with Probe-1.

Figure 5:
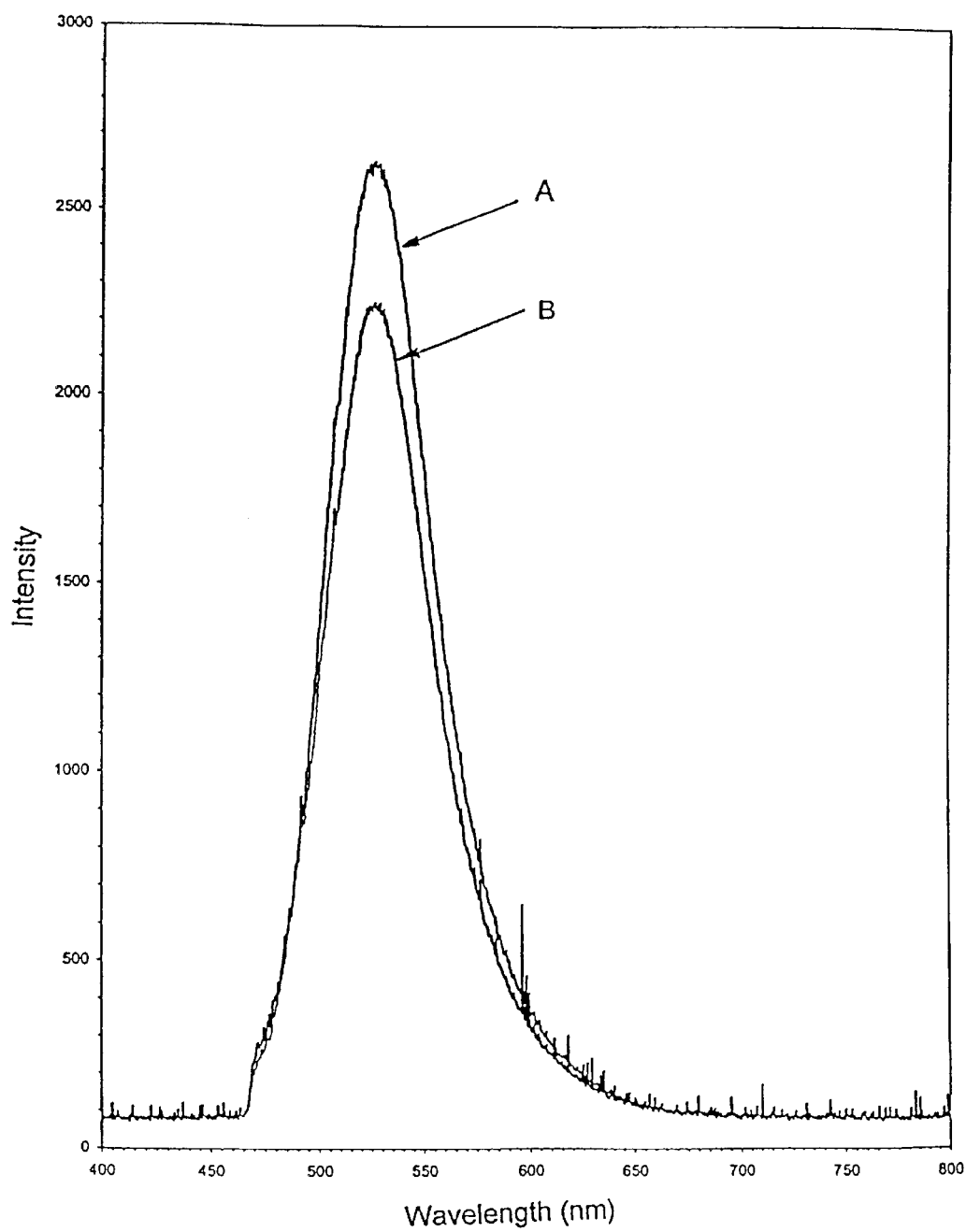

FIG. 5 shows the results of ssDNA-1 hybridization on the double-layer partition assembly. Curve A corresponds to the solution obtained from the bottom membrane (perfect match) and Curve B corresponds to the solution obtained from the top membrane (one base mismatch). The peak intensity of Curve A (perfect match) is higher than that of Curve B (one base mismatch).

Examples 6A–6C

In each of Examples 6A–6C, Probe-1 was covalently bound to a membrane. 100 pmol of target ssDNA with a fluorescent tag were driven forward and backward to pass through the membrane six times (i.e., through three forward/backward cycles) by electrophoresis in an 8% polyacrylamide gel.

The following target sequences were used in the Examples:
Example 6A ssDNA-1
Example 6B ssDNA-2
Example 6C ssDNA-4

Figure 6:
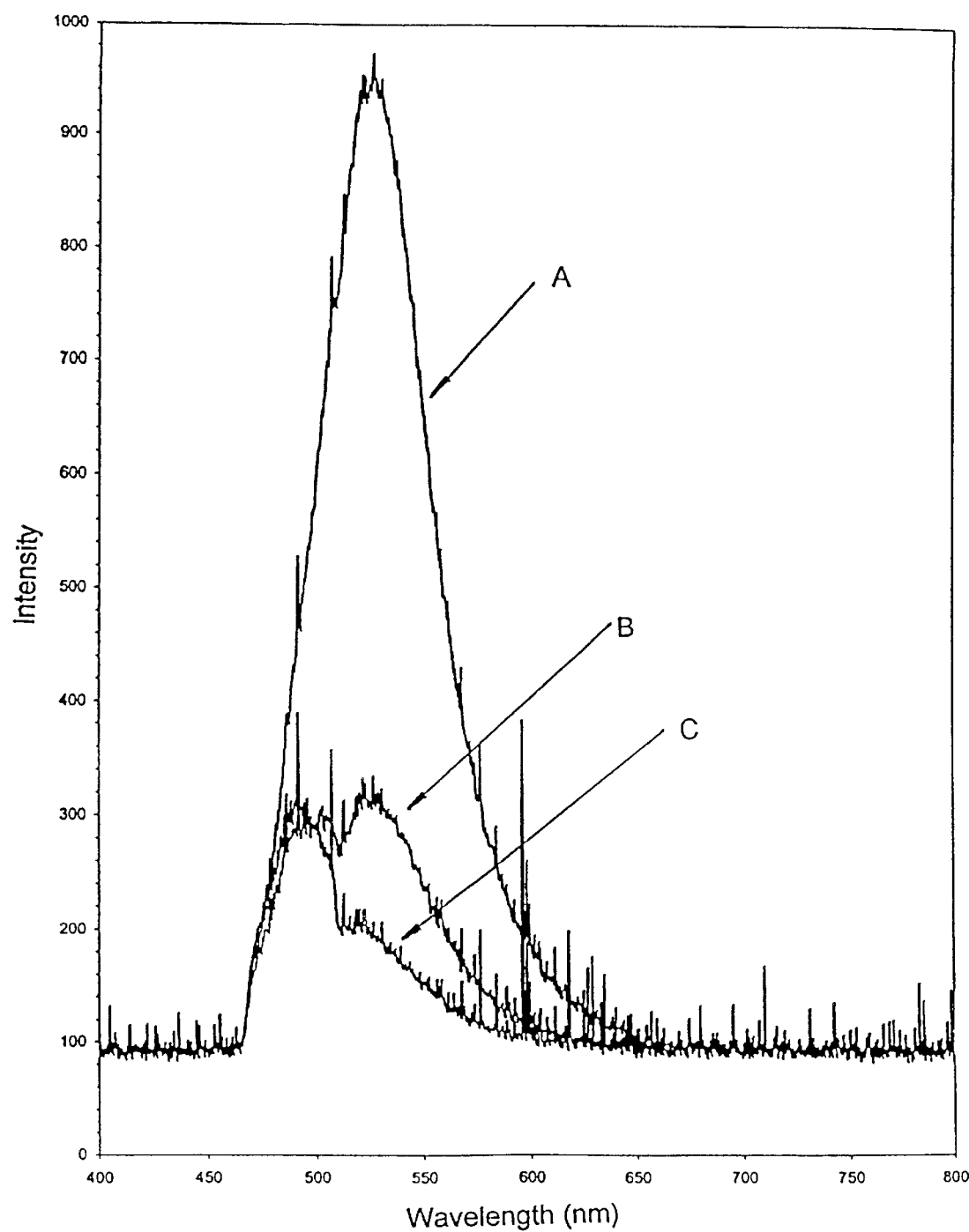

FIG. 6 shows the results from Examples 6A–6C. The perfectly matched probe and target of Example 6A generated a solution having the highest intensity; the one base mismatched pair of Example 6B yielded the second highest intensity; and the three base mismatched pair of Example 6C yielded the lowest intensity.

Examples 7A–7B

In each of Examples 7A and 7B, Probe-1 was covalently bound to a membrane. 100 pmol of target ssDNA with a fluorescent tag were driven forward and backward to pass through the membrane six times (i.e., through three forward/backward cycles) by electrophoresis in an 1.4% agarose gel.

The following target sequences were used in the examples:
Example 7A ssDNA-1
Example 7B ssDNA-2

Figure 7:
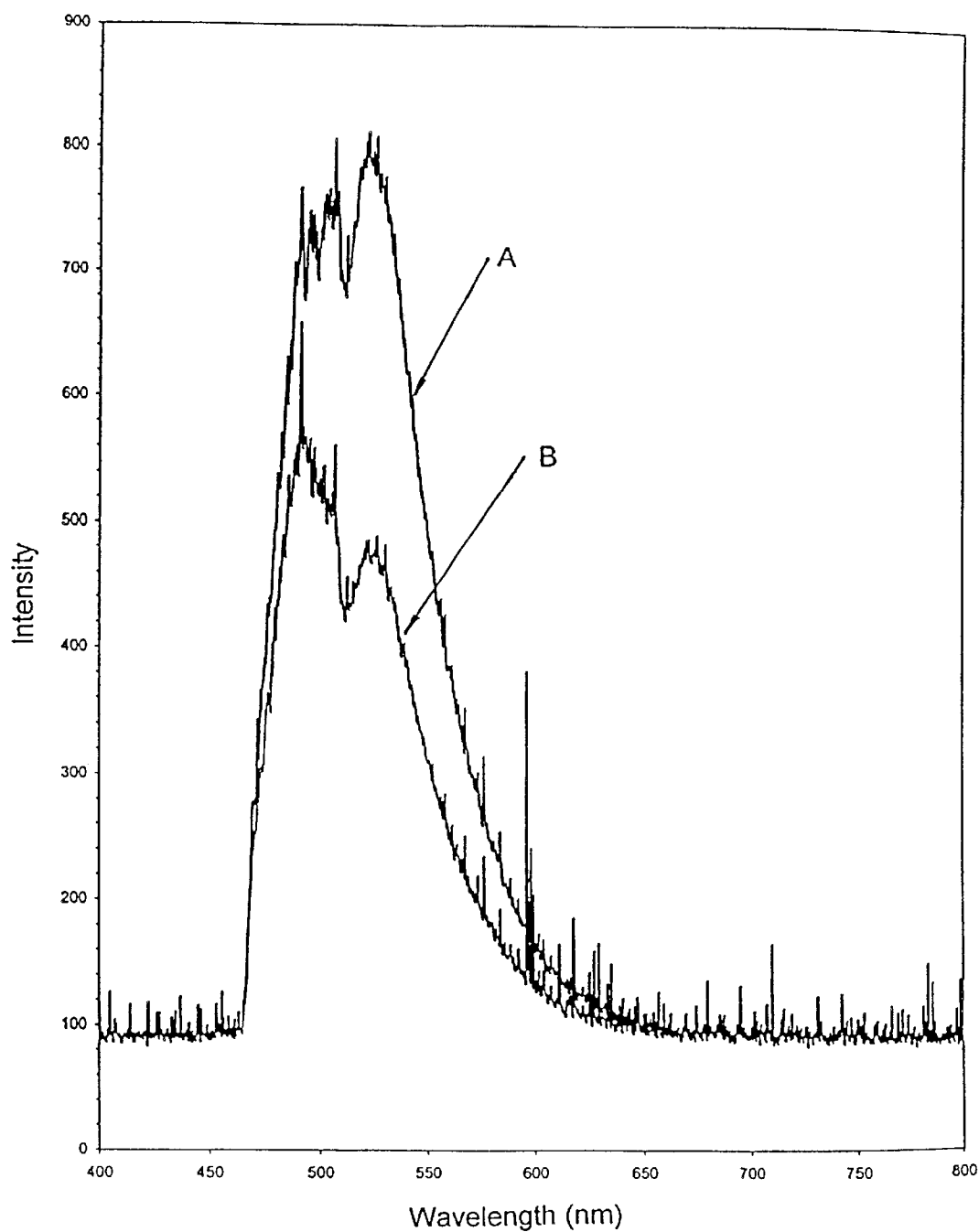

FIG. 7 shows the results from Examples 7A and 7B. The perfectly matched probe and target of Example 7A generated a solution having the higher intensity, whereas the one base mismatched pair of Example 7B yielded a solution having the lower intensity.

Examples 8A–8C

In these examples, target dsDNA was hybridized with Probe-1 covalently bound to membranes.

20 μl (100 pmol) dsDNA was added to 30 μl 0.5×TBE buffer, heated to 95° C. for one minute and immediately cooled in ice water for one minute. The cooled solution was immediately added on the probe-labeled membrane and spun at 5000 rpm for 1 minute at room temperature. The filtrate was collected, heated, cooled, added to the membrane and centrifuged. This procedure was repeated until the original solution/filtrate had passed through the membrane six times.

The membrane was separated from its container and washed with deionized water to remove non-specifically binding entities. The washed membrane was immersed in 100 μl of a 0.2 N sodium hydroxide solution at room temperature for ten minutes to denature the nucleic acid sequences.

The resulting solution was transferred to a cuvette for fluorescent analysis according to our earlier applications, as discussed above.

Figure 8:
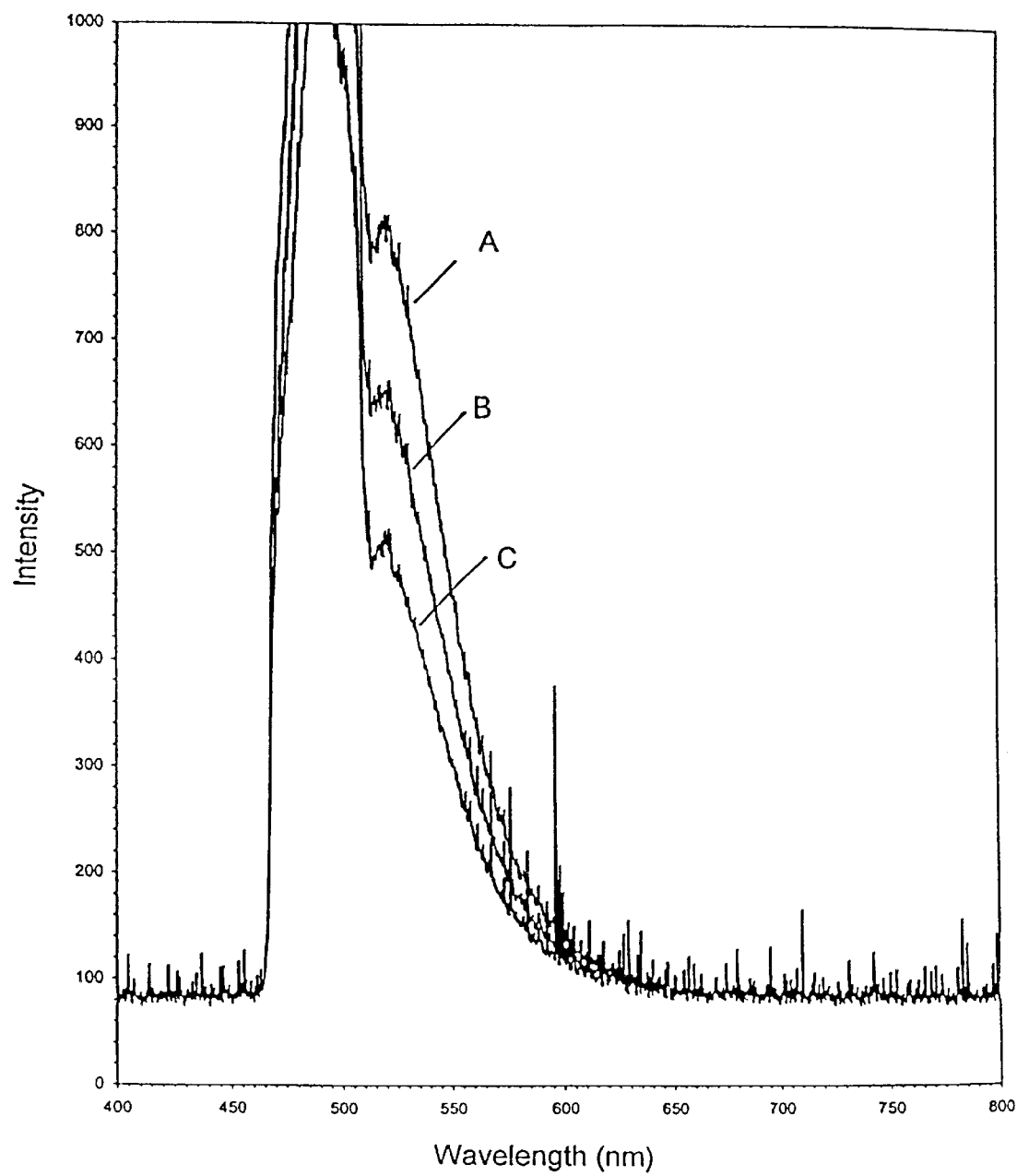

The following dsDNA target sequences were used in the examples:
8A: 5'TT CCG AGA GCT GAA TGA GGC Fluo 3' (SEQ ID NO:8) AA GGC TCT CGA CTT ACT CCG
8B: 5' TT CCG AGA GCA GAA TGA GGC Fluo 3' (SEQ ID NO:9) AA GGC TCT CGT CTT ACT CCG
8C: 5' TT CCG AGA GGA GAA TGA GGC Fluo 3' (SEQ ID NO:10) AA GGC TCT CCT CTT ACT CCG FIG. 8 shows the results from Examples 8A–8C. The perfectly matched probe and target of Example 8A generated a solution having the highest intensity; the one base mismatched pair of Example 8B yielded the second highest intensity; and the two base mismatched pair of Example 8C yielded the lowest intensity.

Examples 9A–9D

The following 40mer ssDNAs were prepared:
ssDNA-6: 5'-Fluo-CCT CGA GAT GTT CCG AGA GCT GAA TGA GGC CTT GGA ACT C 3' (SEQ ID NO:11)
ssDNA-7: 5'-Fluo-CTT CGA GAT GTT CCG AGA GCA GAA TGA GGC CTT GGA ACT C 3' (SEQ ID NO:12)
ssDNA-8: 5'-Fluo-CTT CGA GAT GTT CCG AGA GTA CAA TGA GGC CTT GGA ACT C 3' (SEQ ID NO:13)
ssDNA-9: 5'-Fluo-TCC TCT CCC CAG CCA AAG AAG AAA CCA CTG GAT GGA GAA T 3' (SEQ ID NO:14)

Covalent binding of Probe to MemSyn Disks

Carboxy-dTs (Glen Research) were coupled to MemSyn disks (PerSeptive Biosystems) by using a DNA synthesizer (Expetide 8909, PerSeptive Biosystems) according to the protocols of the manufacturer.

These disks were acidified by rinsing with a 0.1 M HCl solution, followed by washing with deionized water. The disks were then loaded with a 0.5 M sodium bicarbonate buffer solution containing a concentration of 10 μM Probe-1 (SEQ ID NO:1) and incubated for 16 hours. After washing away unbound oligonucleotides with PBS/Tween buffer and deionized water, the disks were quenched with 0.1 N NaOH solution for 10 minutes. Finally, the disks were washed with deionized water and dried by air for immediate application, or stored at −20° C.

Hybridization

100 μl (100 pmol) of the target DNA and 200 μl 0.5×TBE buffer were applied to each disk to which the probe had already been covalently bound. Luer slip syringes (1 ml) were then attached to each end of the disk, and the target DNA and buffer were driven through the disks by using the syringes to push the solution back and forth twenty times. The hybridization temperature was maintained at room temperature.

Post-hybridization

After hybridization, each disk was washed three times with 2.5 M TMAC solution and four times with deionized water. A 140 μl solution of 0.2 M NaOH was then passed back and forth through each disk and transferred to a cuvette for fluorescent detection.

Figure 9:
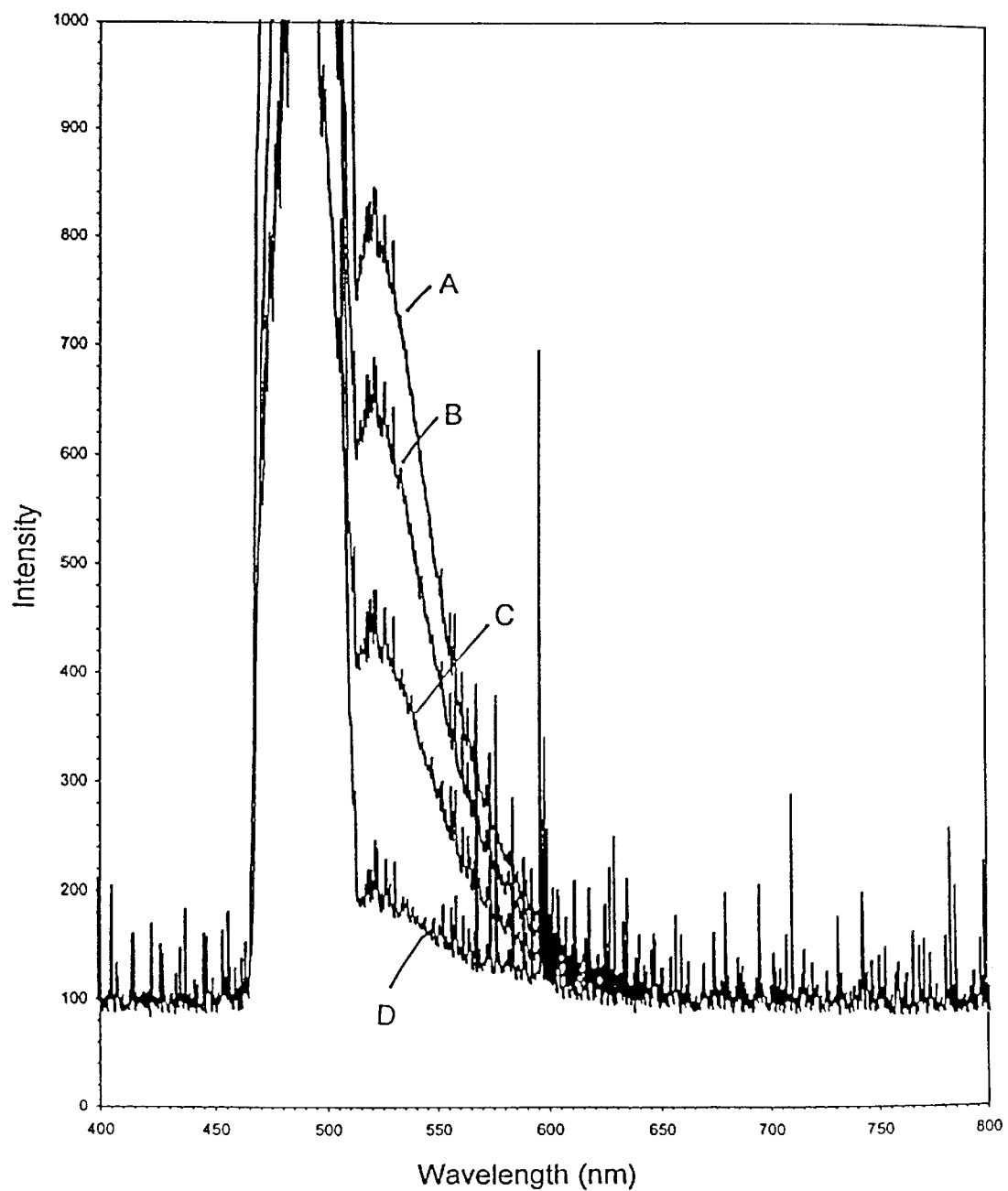

FIG. 9 shows the results of 40mer ssDNA hybridization on MemSyn disks covalently bound with Probe-1.

The following target sequences were used in the Examples:
Example 9A ssDNA-6
Example 9B ssDNA-7
Example 9C ssDNA-8
Example 9D ssDNA-9

FIG. 9 shows the results from Examples 9A–9D. The perfectly matched probe and target of Example 9A generated a solution having the highest intensity; the one base mismatched pair of Example 9B yielded the second highest intensity; the three base mismatched pair of Example 9C yielded the third highest intensity, and the non-target sequence of Example 9D yielded the lowest intensity.

Examples 10A–10D

Covalent binding of Probe to Columns

Carboxy-dTs (Glen Research) were coupled to CPG columns (PerSeptive Biosystems) by using a DNA synthesizer (Expetide 8909, PerSeptive Biosystems) according to the protocols of the manufacturer.

These CPG columns were acidified by rinsing with a 0.1 M HCl solution, followed by washing with deionized water. The columns were then loaded with a 0.5 M sodium bicarbonate buffer solution containing a concentration of 10 $\mu$M Probe-1 (SEQ ID NO:1) and incubated for 16 hours. After washing away unbound oligonucleotides with PBS/Tween buffer and deionized water, the columns were quenched with 0.1 N NaOH solution for 10 minutes. Finally, the columns were washed with deionized water and dried by air for immediate application, or stored at –20° C.

Hybridization

100 $\mu$l (100 pmol) of the target DNA and 200 $\mu$l 0.5×TBE buffer were applied to each column to which the probe had already been covalently bound. The target and buffer were then driven through the column twice by a centrifuger at 900 rpm for 20 seconds. The hybridization temperature was maintained at room temperature.

Post-hybridization

After hybridization, each column was washed three times with 2.5 M TMAC solution and four times with deionized water. A 140 $\mu$l solution of 0.1 M NaOH was then passed through each column and transferred to a cuvette for fluorescent detection.

The following target sequences were used in the Examples:

Example 10A ssDNA-6

Example 10B ssDNA-7

Example 10C ssDNA-8

Example 10D ssDNA-6

All of these examples used a column having Probe-1 loaded on it, except Example 10D, which used a negative control column without any probe.

Figure 10:
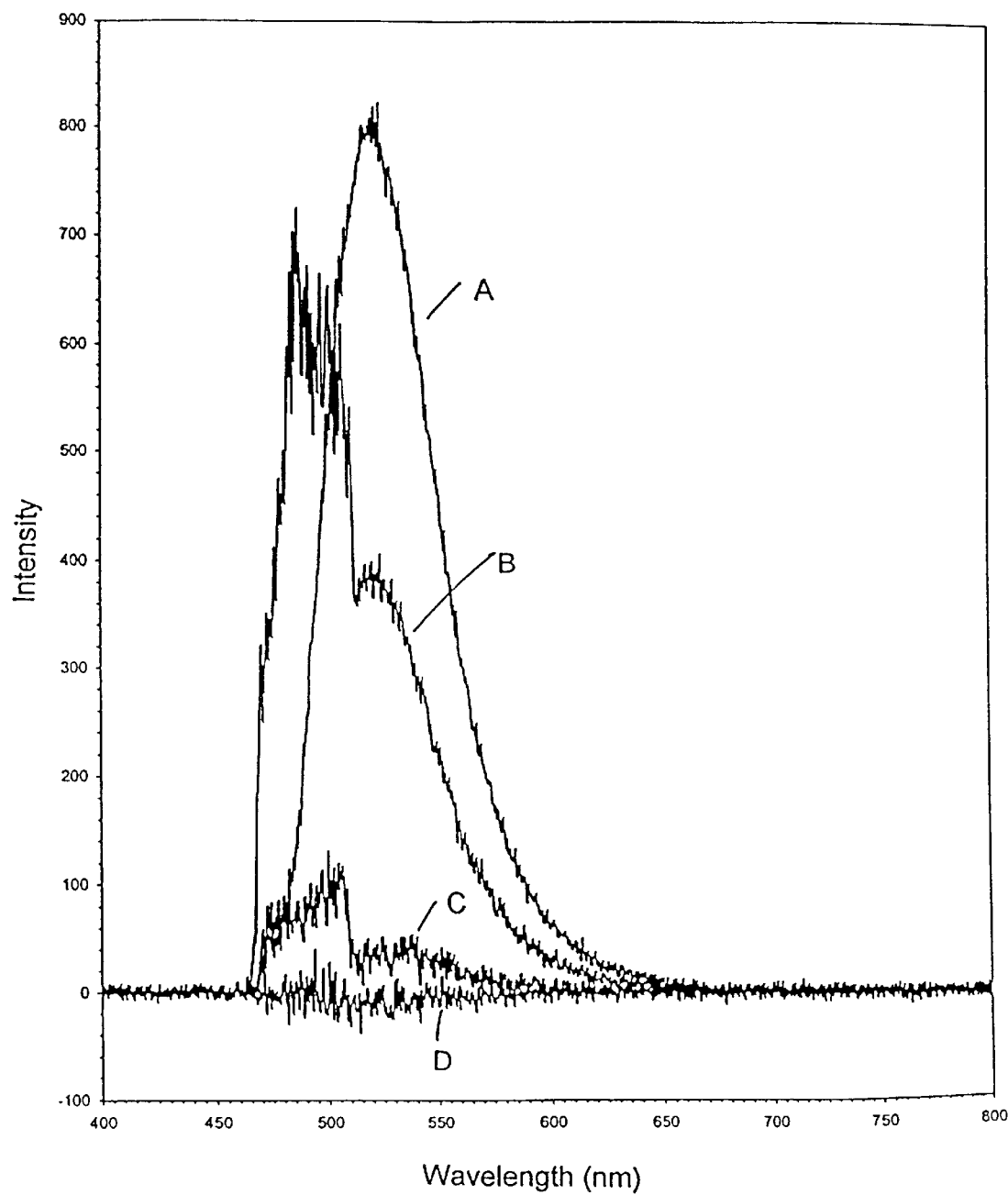

FIG. 10 shows the results from Examples 10A–10D. The perfectly matched probe and target of Example 10A generated a solution having the highest intensity; the one base mismatched pair of Example 10B yielded the second highest intensity; the three base mismatched pair of Example 10C yielded the third highest intensity, and the target sequence without a probe of Example 10D yielded the lowest intensity.

While the invention has been described in detail and with reference to specific examples thereof, it will be apparent to one skilled in the art that various changes and modifications can be made therein without departing from the spirit and scope thereof.

---

What is claimed is:

1. A method for hybridizing nucleobase-containing sequences, said method comprising:
   providing a partition assembly having first nucleobase-containing sequence bound thereto;
   exposing said partition assembly to unbound second nucleobase-containing sequences;
   applying a force to drive said unbound second nucleobase-containing sequences through said partition assembly; and
   hybridizing said unbound second nucleobase-containing sequences to said bound first nucleobase-containing sequences to form hybridization complexes.

2. The method of claim 1, wherein said force is at least one member selected from the group consisting of centrifugal force, electrophoretic force, gravitational force, vacuum and pressure.

3. The method of claim 2, wherein said first nucleobase-containing sequence are probes and said second nucleobase-containing sequences are targets.

4. The method of claim 3, further comprising:
separating non-specifically binding targets from said hybridization complexes and said partition assembly;
de-hybridizing said hybridization complexes to release targets therefrom;
collecting said de-hybridized targets in a fluid medium; and
measuring a signal proportional to a concentration of said de-hybridized target in said liquid medium to assay for said targets.

5. The method of claim 4, wherein said signal is a fluorescent emission having a wavelength of about 400 to about 1000 nm, which is generated by irradiating fluorophores attached to said targets with a laser beam having a wavelength of about 450 to about 530 nm.

6. The method of claim 4, wherein said targets are distinguished from other targets differing from said targets by only on base.

7. The method of claim 2, wherein said first nucleobase-containing sequences are targets and said second nucleobase-containing sequences are probes.

8. The method of claim 7, further comprising:
separating non-specifically binding probes from said hybridization complexes and said partition assembly;
de-hybridizing said hybridization complexes to release probes therefrom;
collecting said de-hybridized probes in a fluid medium; and
measuring a signal proportional to a concentration of said de-hybridized probes in said liquid medium to assay for said targets.

9. The method of claim 8, wherein said signal is a fluorescent emission having a wavelength of about 400 to about 1000 nm, which is generated by irradiating fluorophores attached to said probes with a laser beam having a wavelength of about 450 to about 530 nm.

10. The method of claim 7, wherein said targets are distinguished from other targets differing from said targets by only one base.

11. The method of claim 3, further comprising measuring a signal proportional to a concentration of said hybridization complexes on said partition assembly to assay for said targets without de-hybridizing said probes and targets.

12. The method of claim 11, wherein said signal is a fluorescent emission having a wavelength of about 400 to about 1000 nm, which is generated by irradiating fluorophores attached to said hybridization complexes with a laser beam having a wavelength of about 450 to about 530 nm.

13. The method of claim 12, wherein said targets are distinguished from other targets differing from said targets by only one base.

14. The method of claim 7, further comprising measuring a signal proportional to a concentration of said hybridization complexes on said partition assembly to assay for said targets without de-hybridizing said probes and targets.

15. The method of claim 14, wherein said signal is a fluorescent emission having a wavelength of about 400 to about 1000 nm, which is generated by irradiating fluorophores attached to said hybridization complexes with a laser beam having a wavelength of about 450 to about 530 nm.

16. The method of claim 15, wherein said targets are distinguished from other targets differing from said targets by only one base.

17. The method of claim 2, wherein just prior to exposing said partition assembly to unbound second nucleobase-containing sequences, said unbound second nucleobase-containing sequences are thermally denatured and cooled to about 0° C., said cooling being sufficiently rapid to substantially maintain said second nucleobase-containing sequences in denatured form for said hybridization to said bound first nucleobase-containing sequences.

18. The method of claim 17, wherein said second nucleobase-containing sequences are thermally denatured by heating to 95° C. for one minute and are cooled to about 0° C. by immersion in an ice water bath for about one minute.

19. The method of claim 3, wherein said targets are double-stranded.

20. The method of claim 7, wherein said targets are double-stranded.

21. The method of claim 2, wherein said unbound second nucleobase-containing sequences are driven through said partition assembly at least two times.

22. The method of claim 2, wherein said exposing, applying and hybridizing steps are conducted in a fluid medium containing unbound second nucleobase-containing sequences, said partition assembly being immersed in said fluid medium.

23. The method of claim 22, wherein said fluid medium is a buffer solution and said force is centrifugal.

24. The method of claim 22, wherein said fluid medium is an electrophoretic gel and said force is electrophoretic.

25. The method of claim 24, wherein said unbound second nucleobase-containing sequences are driven forward and backward through said partition assembly by sequentially applying electrophoretic forces of opposing polarities.

26. The method of claim 2, wherein said second nucleobase-containing sequences are applied to said partition assembly as a moist mass that adheres to said partition assembly, and said force is vacuum force.

27. A method for hybridizing nucleobase-containing sequences, said method comprising:
providing a partition assembly having first nucleobase-containing sequences bound thereto;
exposing said partition assembly to unbound second nucleobase-containing sequences;
applying a force to drive said unbound second nucleobase-containing sequences through said partition assembly, wherein said force is at least one member selected from the group consisting of centrifugal force, electrophoretic force, gravitational force, vacuum and pressure; and
hybridizing said unbound second nucleobase-containing sequences to said bound first nucleobase-containing sequences to form hybridization complexes,
wherein said partition assembly comprises two opposing membranes, a first membrane having said first nucleobase-containing sequences bound thereto and a second membrane having third nucleobase-containing sequences bound thereto, said first and third nucleobase-containing sequences being probes differing from each other by at least one base.

28. The method of claim 27, wherein said first nucleobase-containing sequences are perfectly complementary to at least a segment of said second nucleobase-containing sequences, and said third nucleobase-containing sequences are not perfectly complementary with any segment of said second nucleobase-containing sequences.

29. The method of claim 28, wherein said third nucleobase-containing sequences are perfectly complementary to at least a segment of fourth nucleobase-containing sequences, which differ from said second nucleobase-containing sequences by at least one base, and wherein said second sequences are detected when said liquid medium collected from said first membrane has a higher fluorescent intensity than said liquid medium collected from said second membrane, and said fourth sequences are detected when said liquid medium collected from said second membrane has a higher fluorescent intensity than said liquid medium collected from said first membrane.

30. An apparatus for rapidly assaying nucleobase-containing targets, said apparatus comprising:
- a partition assembly comprising at least one permeable or semi-permeable partition, wherein nucleobase-containing probe sequences are bonded to said at least one partition and said at least one partition is sufficiently porous to allow said targets to pass therethrough;
- force-generating means for driving said targets through said partition assembly;
- a laser for inducing fluorophores on said targets to fluoresce;
- a fluorescence detector;
- a data recorder; and
- a data display device.

31. An apparatus for rapidly assaying nucleobase-containing target sequences, said apparatus comprising:
- a partition assembly comprising at least one permeable or semi-permeable partition, wherein nucleobase-containing target sequences are bonded to said at least one partition and said at least one partition is sufficiently porous to allow probes to pass therethrough;
- force-generating means for driving said probes through said partition assembly;
- a laser for inducing fluorophores on said probes to fluoresce;
- a fluorescence detector;
- a data recorder; and
- a data display device.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 18 bases
      (B) TYPE: nucleotide
      (C) STRANDEDNESS: single-stranded
      (D) TOPOLOGY: linear (xi) SEQUENCE DESCRIPTION: SEQ ID NO: 1:

CCT CAT TCA GCT CTC GGA                18

(2) INFORMATION FOR SEQ ID NO: 2:

(i) SEQUENCE CHARACTERISTICS:
      (A) LENGTH: 18 bases
      (B) TYPE: nucleotide
      (C) STRANDEDNESS: single-stranded
      (D) TOPOLOGY: linear (xi) SEQUENCE DESCRIPTION: SEQ ID NO: 2:

CCT CAT TCT GCT CTC GGA                18

(2) INFORMATION FOR SEQ ID NO: 3:

(i) SEQUENCE CHARACTERISTICS:
      (A) LENGTH: 18 bases
      (B) TYPE: nucleotide
      (C) STRANDEDNESS: single-stranded
      (D) TOPOLOGY: linear (xi) SEQUENCE DESCRIPTION: SEQ ID NO: 3:

TCC GAG AGC TGA ATG AGG                                          18

(2) INFORMATION FOR SEQ ID NO: 4:

(i) SEQUENCE CHARACTERISTICS:
        (A) LENGTH: 18 bases
        (B) TYPE: nucleotide
        (C) STRANDEDNESS: single-stranded
        (D) TOPOLOGY: linear (xi) SEQUENCE DESCRIPTION: SEQ ID NO: 4:

TCC GAG AGC AGA ATG AGG                                          18

(2) INFORMATION FOR SEQ ID NO: 5:

(i) SEQUENCE CHARACTERISTICS:
        (A) LENGTH: 18 bases
        (B) TYPE: nucleotide
        (C) STRANDEDNESS: single-stranded
        (D) TOPOLOGY: linear (xi) SEQUENCE DESCRIPTION: SEQ ID NO: 5:

TCC GAG AGA AGA ATG AGG                                          18

(2) INFORMATION FOR SEQ ID NO: 6:

(i) SEQUENCE CHARACTERISTICS:
        (A) LENGTH: 18 bases
        (B) TYPE: nucleotide
        (C) STRANDEDNESS: single-stranded
        (D) TOPOLOGY: linear (xi) SEQUENCE DESCRIPTION: SEQ ID NO: 6:

TCC GAG AGT ACA ATG AGG                                          18

(2) INFORMATION FOR SEQ ID NO: 7:

(i) SEQUENCE CHARACTERISTICS:
        (A) LENGTH: 18 bases
        (B) TYPE: nucleotide
        (C) STRANDEDNESS: single-stranded
        (D) TOPOLOGY: linear (xi) SEQUENCE DESCRIPTION: SEQ ID NO: 7:

TCC TCT CCC CAG CCA AAG                                          18

(2) INFORMATION FOR SEQ ID NO: 8:

(i) SEQUENCE CHARACTERISTICS:
        (A) LENGTH: 20 bases
        (B) TYPE: nucleotide
        (C) STRANDEDNESS: double-stranded
        (D) TOPOLOGY: linear (xi) SEQUENCE DESCRIPTION: SEQ ID NO: 8:

TTC CGA GAG CTG AAT GAG GC                                       20
AAG GCT CTC GAC TTA CTC CG (2) INFORMATION FOR SEQ ID NO: 9:

(i) SEQUENCE CHARACTERISTICS:
        (A) LENGTH: 20 bases
        (B) TYPE: nucleotide
        (C) STRANDEDNESS: double-stranded
        (D) TOPOLOGY: linear (xi) SEQUENCE DESCRIPTION: SEQ ID NO: 9:

```
TTC CGA GAG CAG AAT GAG GC                                          20
AAG GCT CTC GTC TTA CTC CG (2) INFORMATION FOR SEQ ID NO: 10:

(i) SEQUENCE CHARACTERISTICS:
        (A) LENGTH: 20 bases
        (B) TYPE: nucleotide
        (C) STRANDEDNESS: double-stranded
        (D) TOPOLOGY: linear (xi) SEQUENCE DESCRIPTION: SEQ ID NO: 10:

TTC CGA GAG GAG AAT GAG GC                                          20
AAG GCT CTC CTC TTA CTC CG (2) INFORMATION FOR SEQ ID NO: 11:

(i) SEQUENCE CHARACTERISTICS:
        (A) LENGTH: 40 bases
        (B) TYPE: nucleotide
        (C) STRANDEDNESS: single-stranded
        (D) TOPOLOGY: linear (xi) SEQUENCE DESCRIPTION: SEQ ID NO: 11:

CCTCGAGATG TTCCGAGAGC TGAATGAGGC CTTGGAACTC                          40

(2) INFORMATION FOR SEQ ID NO: 12:

(i) SEQUENCE CHARACTERISTICS:
        (A) LENGTH: 40 bases
        (B) TYPE: nucleotide
        (C) STRANDEDNESS: single-stranded
        (D) TOPOLOGY: linear (xi) SEQUENCE DESCRIPTION: SEQ ID NO: 12:

CTTCGAGATG TTCCGAGAGC AGAATGAGGC CTTGGAACTC                          40

(2) INFORMATION FOR SEQ ID NO: 13:

(i) SEQUENCE CHARACTERISTICS:
        (A) LENGTH: 40 bases
        (B) TYPE: nucleotide
        (C) STRANDEDNESS: single-stranded
        (D) TOPOLOGY: linear (xi) SEQUENCE DESCRIPTION: SEQ ID NO: 13:

CTTCGAGATG TTCCGAGAGT ACAATGAGGC CTTGGAACTC                          40

(2) INFORMATION FOR SEQ ID NO: 14:

(i) SEQUENCE CHARACTERISTICS:
        (A) LENGTH: 40 bases
        (B) TYPE: nucleotide
        (C) STRANDEDNESS: single-stranded
        (D) TOPOLOGY: linear (xi) SEQUENCE DESCRIPTION: SEQ ID NO: 14:

TCCTCTCCCC AGCCAAAGAA GAAACCACTG GATGGAGAAT                          40
```